United States Patent [19]

Goldmann et al.

[11] Patent Number: 4,628,107
[45] Date of Patent: Dec. 9, 1986

[54] INTERMEDIATE 8-CARBOXALDEHYDE-(-CHROMONE AND -THIOCHROMONE) DERIVATIVES

[75] Inventors: Siegfried Goldmann; Gerhard Franckowiak, both of Wuppertal; Matthias Schramm, Cologne; Günter Thomas; Rainer Gross, both of Wuppertal, all of Fed. Rep. of Germany

[73] Assignee: Bayer Aktiengesellschaft, Leverkusen, Fed. Rep. of Germany

[21] Appl. No.: 750,571

[22] Filed: Jun. 28, 1985

Related U.S. Application Data

[63] Continuation-in-part of Ser. No. 589,436, Mar. 14, 1984, Pat. No. 4,540,789, and a continuation-in-part of Ser. No. 589,615, Mar. 14, 1984, abandoned.

[30] Foreign Application Priority Data

Mar. 25, 1983 [DE] Fed. Rep. of Germany ....... 3311004
Mar. 25, 1983 [DE] Fed. Rep. of Germany ....... 3311005

[51] Int. Cl.$^4$ ................. C07D 405/06; C07D 405/12; C07D 409/06; C07D 409/12
[52] U.S. Cl. ........................ 549/23; 546/269; 546/274; 549/60; 549/401; 549/403; 548/525
[58] Field of Search ............... 549/23, 60, 401, 402, 549/403; 546/269, 274; 548/525

[56] References Cited

FOREIGN PATENT DOCUMENTS 0059883 4/1982 Japan ..................... 549/402

Primary Examiner—Henry R. Jiles
Assistant Examiner—J. G. Mullins
Attorney, Agent, or Firm—Sprung, Horn, Kramer & Woods

[57] ABSTRACT

Novel chromone-8-aldehydes and thiochromone-8-aldehydes, useful in making pharmaceutically active dihydropyridines, of the formula

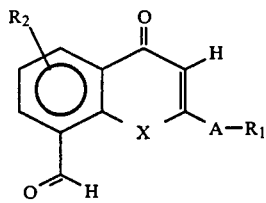

in which
$R_1$ represents hydrogen, a $C_1$-$C_{10}$ aliphatic hydrocarbon radical, a $C_1$-$C_{10}$ alkyl carboxylate, or an aromatic or heteroaromatic ring which optionally has 1-5 identical or different halogen, $C_1$-$C_{10}$-alkyl, $C_1$-$C_{10}$-alkoxy, $C_1$-$C_{10}$-alkylthio, $C_1$-$C_{10}$-alkylsulphinyl, cyano, hydroxyl, nitro, $C_1$-$C_5$-monofluoroalkyl or polyfluoroalkyl, $C_1$-$C_5$ monofluoroalkoxy or polyfluoroalkoxy, $C_1$-$C_6$ monofluoroalkylthio or polyfluoroalkylthio, amino, $C_1$-$C_5$-monoalkylamino or $C_1$-$C_5$ dialkylamino substituents,
$R_2$ represents hydrogen or 1 to 3 halogen atoms, A represents a single bond, a $C_1$-$C_{20}$ alkylene chain or a $C_2$-$C_{20}$ alkylene chain which can optionally be interrupted by oxygen or sulphur, and
X represents oxygen or sulphur, are made from corresponding compounds which in 8-position carry an ester or olefinic radical.

8 Claims, No Drawings

INTERMEDIATE 8-CARBOXALDEHYDE-(-CHROMONE AND -THIOCHROMONE) DERIVATIVES

This is a continuation-in-part of Ser. No. 589,436, filed Mar. 14, 1984, now U.S. Pat. No. 4,540,789 and Ser. No. 589,615 filed Mar. 14, 1984, now abandoned.

The present invention relates to new 1,4-dihydropyridines, several processes for their preparation and their use in medicaments, in particular in medicaments which influence the circulation, as well as new intermediates therefor.

Thiochromones having the structure I are producible by condensation of thiophenols with benzoylacetic esters in polyphosphoric acid (Bossert, Lieb. Ann. 680, 40 (1964)).

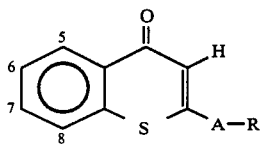

The corresponding 8-formyl derivatives are not producible by this route.

Furthermore, the preparation of chromones from 2-hydroxyphenyl ketones and acid chlorides or esters in the presence of base is known (J. Staunton in Barton, Ollis, Comprehensive Organic Chemistry, Pergamon Press, Oxford 1979, Volume 4, page 678).

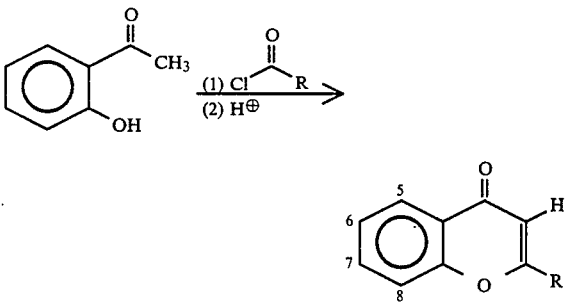

However, the corresponding 8-aldehydes are not producible by these routes since, under the same conditions, the corresponding coumarins are formed from 2-hydroxybenzaldehydes (J. Staunton, see above, page 651).

The new dihydropyridines are characterized by the following general formula I,

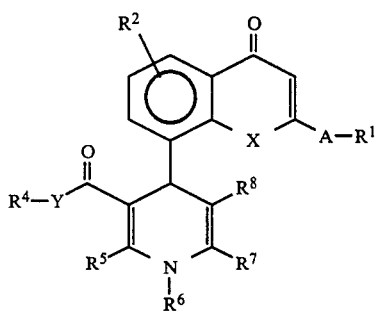

in which $R^1$ represents hydrogen, a straight-chain, cyclic of branched aliphatic hydrocarbon radical with 1 to 10 C atoms, a carboxylic acid alkyl ester (alkyl radical with 1 to 10 C atoms in the alkyl chain), or an aromatic or heteroaromatic radical which is optionally substituted by one to 5 identical or different substituents from the group comprising halogen, alkyl (1 to 10 C atoms), alkoxy (1 to 10 C atoms), alkylthio (1 to 10 C atoms), alkylsulphinyl (1 to 10 C atoms), cyano, hydroxyl, nitro, mono- or poly-fluoroalkyl (1 to 5 C atoms), mono- or poly-fluoroalkoxy (1 to 5 C atoms), mono- or poly-fluoroalkylthio (1 to 5 C atoms), amino, monoalkylamino (1 to 5 C atoms) and dialkylamino (in each case 1 to 5 C atoms), $R^2$ represents 1 to 3 halogen atoms or hydrogen, $R^4$ represents a straight-chain, branched or cyclic, saturated or unsaturated hydrocarbon radical with 1 to 20 C atoms, which is optionally substituted by alkoxy (with 1 to 10 C atoms), alkylthio (with 1 to 10 C atoms), alkylsulphinyl (with 1 to 10 C atoms), trialkylsilyl (with in each case 1 to 6 C atoms), halogen, cyano, hydroxyl, amino, alkylamino (with 1 to 6 C atoms), dialkylamino (with in each case 1 to 6 C atoms), morpholinyl, piperidyl, piperazinyl, nitro, nitrate, aryl or heteroaryl, whereby the aryl- or heteroarylradical can optionally be substituted by 1 to 3 identical or different substituents from the group comprising halogen, alkyl (with 1 to 6 C atoms), alkoxy (with 1 to 6 C atoms), alkylthio (with 1 to 6 C atoms), alkylsulphinyl (with 1 to 6 C atoms), alkylsulphonyl (with 1 to 6 C atoms), hydroxyl, cyano, nitro, amino, alkylamino (with 1 to 6 C atoms), dialkylamino (with in each case 1 to 6 C atoms), mono- or poly-fluoroalkyl (with 1 to 6 C atoms) and mono- or poly-fluoroalkoxy (with 1 to 6 C atoms), $R^5$ and $R^7$ can be identical or different and represents hydrogen or a straight-chain, branched or cyclic, saturated or unsaturated aliphatic alkyl radical (1 to 10 C atoms), which optionally contains one or two identical or different hetero chain members from the group comprising O, CO, NH, N-alkyl (1 to 8 C atoms), S and $SO_2$, and is optionally substituted by halogen, nitro, cyano, azido, hydroxyl, aryl, heteroaryl, amino or monoakylamino or dialkylamino (with in each case 1 to 6 C atoms), $R^6$ represents hydrogen or a straight-chain or branched alkyl radical (with 1 to 20 C atoms), which is optionally substituted by alkoxy (with 1 to 10 C atoms), halogen or morpholino, $R^8$ represents hydrogen, nitro, cyano, halogen, alkyl (1 to 4 C atoms), mono- or poly-fluoroalkyl (1 to 4 C atoms) or hydroxycarbonyl, A represents a direct bond, or an alkylene chain (1 to 20 C atoms) or an alkenylene chain (2 to 20 C atoms), the chains being optionally interrupted by O or S, X represents O or S and Y represents a direct bond, O, S, —NH— or N-alkyl (with 1 to 8 C atoms), in the form of isomers, isomer mixtures, racemates and optical antipodes, and their pharmaceutically acceptable salts.

Examples of salts which may be mentioned are hydrochlorides, hydrogen sulphates, sulphates, hydrogen phosphates, acetates, maleates, benzoates, citrates, tartrates and lactates.

Compounds of the general formula (I) which are of particular interest are those in which $R^1$ represents hydrogen, a straight-chain, cyclic or branched aliphatic hydrocarbon radical with 1 to 8 C atoms, a carboxylic acid alkyl ester with 1 to 8 C atoms in the alkyl chain, phenyl, naphthyl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl or quinoxalyl, it being possible for the aryl and heteroaryl radicals mentioned optionally to contain 1 to 5 identical or different substituents from the group comprising fluorine, chlorine, bromine, iodine, alkyl (1 to 8 C atoms), alkylthio (1 to 8 C atoms), alkylsulphinyl (1 to 8 C atoms), cyano, hydroxyl, nitro, mono- or poly-fluoroalkyl (1 to 4 C atoms), mono- or poly-fluoroalkoxy (1 to 4 C atoms), mono- or poly-fluoroalkylthio (1 to 4 C atoms), amino, monoalkylamino (1 to 5 C atoms) and dialkylamino (in each case 1 to 5 C atoms), $R^2$ represents hydrogen or one to three fluorine or chlorine atoms, $R^4$ represents a straight-chain, branched or cyclic saturated or unsaturated hydrocarbon radical with 1 to 18 C atoms, which is optionally substituted by alkoxy (with 1 to 8 C atoms), alkylthio (with 1 to 8 C atoms), alkylsulphinyl (with 1 to 8 C atoms), trialkylsilyl (with in each case 1 to 5 C atoms), Cl, Br, I, F, cyano, hydroxyl, amino, alkylamino (with 1 to 5 C atoms), dialkylamino (with in each case 1 to 5 C atoms), morpholinyl, piperidyl, piperazinyl, nitro, nitrate, phenyl, naphthyl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, indolyl or quinazolyl, it being possible for the aromatics or heteroaromatics mentioned optionally to be substituted by 1 to 3 identical or different substituents from the group comprising F, Cl, Br, alkyl (with 1 to 5 C atoms), alkoxy (with 1 to 5 C atoms), alkylthio (with 1 to 4 C atoms) and alkylsulphinyl (with 1 to 4 C atoms), $R^5$ and $R^7$ can be identical or different and represents hydrogen or a straight-chain, branched or cyclic, saturated or unsaturated aliphatic alkyl radical (1 to 8 C atoms), which optionally contains one or two identical or different hetero chain members from the group comprising O, CO, S and N-alkyl (1 to 6 C atoms), and is optionally substituted by halogen, nitro, cyano, hydroxyl, amino or monoalkylamino or dialkylamino (with in each case 1 to 5 C atoms), $R^6$ represents hydrogen or a straight-chain or branched alkyl radical (with 1 to 16 C atoms), which is optionally substituted by alkoxy (with 1 to 8 C atoms), halogen or morpholino, $R^8$ represents hydrogen, nitro, cyano, fluoride, chlorine, bromine, alkyl (1 to 3 C atoms), mono- or poly-fluoroalkyl (1 to 3 C atoms) or hydroxycarbonyl, A represents a direct bond, or an alkylene chain (1 to 18 C atoms) or an alkenylene chain (2 to 18 C atoms), the chains being optionally interrupted by O or S, X represents O or S and Y represents a direct bond, O, S, —NH— or —N(alkyl)— (with 1 to 6 C atoms).

Compounds of the general formula (I) which may be mentioned as preferred are those in which $R^1$ represents hydrogen, a straight-chain, branched or cyclic aliphatic hydrocarbon radical with 1 to 7 C atoms, a carboxylic acid alkyl ester with 1 to 6 C atoms in the alkyl radical, phenyl, naphthyl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, indolyl, benzmidazolyl or quinoxalyl, it being possible for the aryl and heteroaryl radicals mentioned optionally to contain 1 to 4 identical or different substituents from the group comprising fluorine, chlorine, bromine, alkyl (1 to 6 C atoms), alkylthio (1 to 6 C atoms), alkylsulphinyl (1 to 6 C atoms), cyano, hydroxyl, nitro, mono- or poly-fluoroalkyl (1 to 3 C atoms), mono- or poly-fluoroalkoxy (1 to 3 C atoms), amino, monoalkylamino (1 to 4 C atoms) and dialkylamino (in each case 1 to 4 C atoms), $R^2$ represents hydrogen or one to three fluorine atoms, $R^4$ represents a straight-chain, branched or cyclic, saturated or unsaturated hydrocarbon radical with 1 to 12 C atoms, which is optionally substituted by alkoxy (with 1 to 6 C atoms), alkylthio (with 1 to 6 C atoms), alkylsulphinyl (with 1 to 6 C atoms), trialkylsilyl (with in each case 1 to 3 C atoms), Cl, Br, F, cyano, hydroxyl, amino, alkylamino (with 1 to 4 C atoms), dialkylamino (with in each case 1 to 4 C atoms), morpholinyl, piperidyl, piperazinyl, nitro, nitrate, phenyl, naphthyl, thienyl, furyl, pyrryl, imidazolyl, oxazolyl, thiazolyl, pyridyl, pyrimidyl, pyrazinyl or indolyl, it being possible for the aromatics or heteroaromatics mentioned optionally to be substituted by 1 to 3 identical or different substituents from the group comprising F, Cl, Br, alkyl (with 1 to 4 C atoms), alkoxy (with 1 to 4 C atoms), alkylthio (with 1 to 3 C atoms) and alkylsulphinyl (with 1 to 3 C atoms), $R^5$ and $R^7$ can be identical or different and represents hydrogen or a straight-chain, branched or cyclic, saturated or unsaturated aliphatic alkyl radical (1 to 6 C atoms), which optionally contains one or two identical or different hetero chain members from the group comprising O, CO, S and N-alkyl (1 to 4 C atoms), and which is optionally substituted by halogen, nitro, cyano, hydroxyl, amino or monoalkylamino (with 1 to 4 C atoms) or dialkylamino (with in each case 1 to 4 C atoms), $R^6$ represents hydrogen or a straight-chain or branched alkyl radical (with 1 to 12 C atoms), which is optionally substituted by alkoxy (with 1 to 6 C atoms), halogen or morpholino, $R^8$ represents nitro, cyano, fluorine or chlorine, A represents a direct bond, or an alkylene chain (1 to 16 C atoms) or an alkenylene chain (2 to 14 C atoms), the chains being optionally interrupted by O or S, X represents O or S and Y represents a direct bond, O, S, —NH— or —N(alkyl)— (with 1 to 4 C atoms).

The compounds of the general formula (I) according to the invention can be prepared by a process in which (A) aldehydes of the general formula (II)

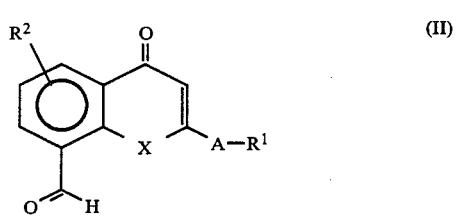

in which $R^1$, $R^2$, A and X have the abovementioned meaning, are reacted with enamines of the general formula (III)

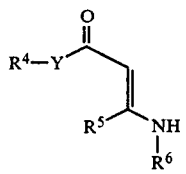

in which $R^4$, $R^5$, $R^6$ and Y have the abovementioned meaning, and ketones of the general formula (IV)

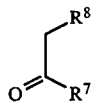

in which $R^7$ and $R^8$ have the abovementioned meaning, if appropriate in the presence of an inert organic solvent at temperatures between 20° and 150° C. or (B) aldehydes of the general formula (II) in which $R^1$, $R^2$, A and X have the abovementioned meaning, are reacted with ketones of the general formula (V)

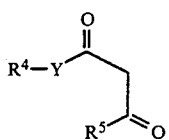

in which $R^4$, $R^5$ and Y have the abovementioned meaning, and enamines of the general formula (VI)

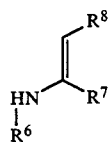

in which $R^6$, $R^7$ and $R^8$ have the abovementioned meaning, if appropriate in the presence of inert organic solvents at temperatures between 20° and 150° C., or (C) ylidene compounds of the general formula (VII)

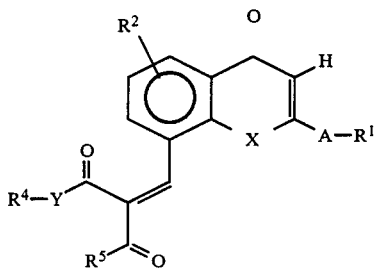

in which $R^1$, $R^2$, $R^4$, $R^5$, A, X and Y have the abovementioned meaning,
are reacted with enamines of the general formula (VI) in which $R^6$, $R^7$ and $R^8$ have the abovementioned meaning, if appropriate in the presence of inert organic solvents at temperatures between 20° and 150° C. or, (D) benzylidene compounds of the general formula (VIII)

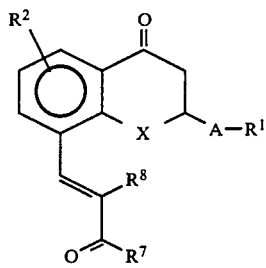

in which $R^1$, $R^2$, $R^7$, $R^8$, A and X have the above mentioned meaning, are reacted with enamines of the general formula (III) in which $R^4$, $R^5$, $R^6$ and Y have the abovementioned meaning, if appropriate in inert organic solvents at temperatures between 20° and 150° C.

Process variant A is preferred if the radical $R^8$ represents nitro, process variants B and C are preferred if the radical $R^8$ represents nitrile, and the process variant D is preferred if the radical $R^8$ has the remaining meanings.

The reactants can be used in any desired proportions relative to one another, but equimolar amounts are preferred. The compounds of the formulae III or IV in process variant A, the compounds of the formulae V or VI in process variant B, the compounds of the formula VI in process variant C and compound of the formula III in process variant D can also be employed in an excess of up to 3 moles.

The reaction temperatures in all process variants are preferably 30° to 120° C., in particular the boiling points of the solvents used.

If the reaction is carried out in the presence of organic solvents, all the inert solvents are suitable, such as, for example, alcohols, acetic acid, benzene and/or toluene.

The aldehydes of the formula II used for the preparation are new and can be prepared, if X=S, by reducing thiochromones of the formula in which $R_1$, $R_2$ and A have the meanings already mentioned, to benzyl alcohols and oxidizing the benzyl alcohol to aldehydes with oxidizing agents.

The thiochromones used as starting substances are known, or they can be prepared by known processes (Bossert, Lieb. Ann. 680, 40 (1964)).

Inert organic solvents can be used for the reduction to the benzyl alcohol, for example ethers, such as, for example, dioxane, diethyl ether, tetrahydrofuran or dimethoxyethane, or aromatics, such as, for example, toluene or benzene. Examples of reducing agents which may be mentioned are alkali metal aluminum hydrides, such as, for example, LiAlH$_4$, or alkyl-aluminum hydrides, such as, for example, diisobutyl-aluminum hydride.

This process is preferably carried out in a temperature range from $-100°$ C. to $+60°$ C., in particular in a range from $-60°$ C. to $+30°$ C.

The reaction is usually carried out under normal pressure, but can also be carried out under increased pressure.

The reducing agent is added in amounts customary to the expert, preferably in amounts of at least four and at most 8 equivalents of hydride.

The same solvents as used in the reduction can be used for the oxidation of the benzyl alcohol to the aldehyde, and in addition halogenated hydrocarbons, such as chloroform and methylene chloride, or ketones, such as, for example, acetone.

The transition metal oxides usually employed for oxidations, but preferably manganese dioxide, can be used as the oxidizing agent.

The oxidation is usually carried out in a temperature range from $-30°$ to $+200°$ C., preferably at the boiling point of the particular solvent.

The oxidation is usually carried out under normal pressure, but can also be carried out under increased pressure.

The oxidizing agent can be employed in amounts of 3 to 20, preferably 5 to 10, oxidation equivalents. It may also be advantageous to add fresh oxidizing agent to the reaction mixture from time to time.

When methyl thioflavone-8-carboxylate is used as the starting material, then the course of the reaction can be represented by the diagram below:

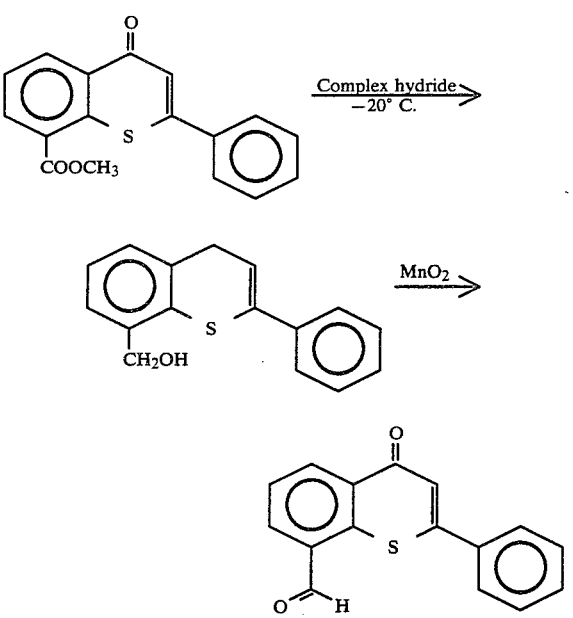

If X=0, chromones of the formula

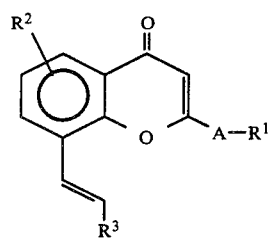

in which

R$^1$, R$^2$ and A have the abovementioned meaning, with the restriction that A is not an alkenylene chain nor contains sulphur and R$^3$ represents hydrogen or alkyl (with 1 to 10 C atoms), are reacted with ozone in the presence of inert organic solvents and the mixture is then worked up by reduction.

The 8-alkenylchromones used as starting substances are known or can be prepared by known processes (U.S. Pat. No. 3,350,411, compare also Synthesis 1982, 221).

Inert solvents which may be mentioned for the ozonolysis are: chlorinated hydrocarbons, such as, for example, methylene chloride, chloroform or carbon tetrachloride, esters, such as, for example, ethyl acetate, alcohols, such as, for example, methanol or ethanol and acids, such as, for example, formic acid or acetic acid.

The ozonolysis is carried out at $-100°$ C. to 20° C., but preferably at $-80°$ C. to $-30°$ C., with subsequent working up by reduction, for example with dimethyl sulphide, with zinc dust, by catalytic hydrogenation or with sodium dithionite.

Only one mole of ozone is used per mole of chromone, in order to prevent splitting of further double bonds.

When 2-cyclohexyl-8-propenylchromone is used, then the course of the reaction can be represented by the diagram below:

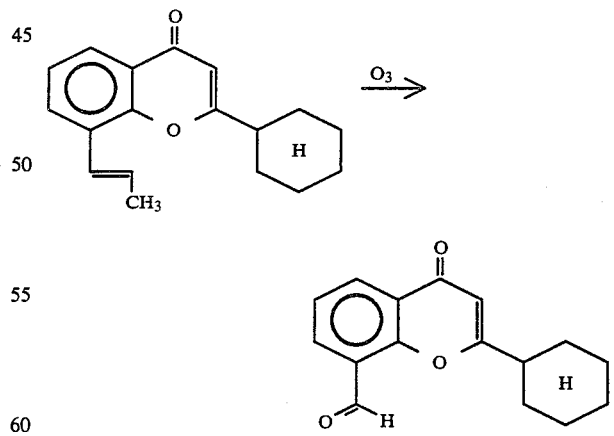

Enamines of the general formula (III) used for the preparation are known and can be prepared by known processes (compare A. C. Cope, J. Am. Chem. Soc. 67, 1017 (1945)).

Keto compounds of the general formula (IV) used for the preparation are known and can be prepared by known processes (J. Org. Chem. 20, 927 (1955)).

Ketones having the structure (V) used for the preparation are known and can be prepared by known processes: for example, if Y=0, D. Borrmann, Umsetzung von Diketen mit Alkoholen, Phenolen und Mercaptanen (Reaction of diketene with alcohols, phenols and mercaptans) in Houben-Weyl, Methoden der Organischen Chemie (Methods of Organic Chemistry), Volume VII, 14, 230 et seq. (1968) and Y. Dikawa, K. Sugano and O. Yonemitsu, J. Org. Chem. 43, 2087 (1978).

Enamines of the general formula (VI) used for the preparation are known and can be prepared by known processes.

The benzylidene compounds having the structure (VII) used for the preparation are new, but can be prepared by known processes (compare G. Jones, "The Knoevenagel Condensation", in Org. Reactions Volume XV, 204 et seq. (1967)).

The compounds according to the invention display a valuable pharmacological action spectrum which could not be predicted. They can be used as cardiotonic agents for improving heart contractility. Moreover, since they increase the flow of $Ca^{++}$ into the cells, they can be used as antihypotonic agents, for lowering the blood sugar level, for detumescing mucous membranes and for influencing the salt and liquid balance.

The compounds according to the invention can be converted in a known manner into the customary formulations, such as tablets, capsules, dragees, pills, granules, aerosols, syrups, emulsions, suspensions and solutions, using inert non-toxic, pharmaceutically suitable excipients or solvents. The therapeutically active compound should in each case be present in a concentration of about 0.5 to 90% by weight of the total mixture, that is to say in amounts which suffice to achieve the dosage range indicated.

The formulations are prepared, for example, by extending the active compounds with solvents and/or excipients, optionally with the use of emulsifiers and/or dispersing agents, and, for example when using water as a diluent, organic solvents can optionally be used as auxiliary solvents.

Examples of auxiliary substances which may be mentioned are: water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid excipients, such as, for example, natural rock powders (for example kaolins, aluminas, talc and chalk), synthetic rock powders (for example highly disperse silica and silicates) and sugars (for example sucrose, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl-sulphate).

Administration is effected in the customary manner, preferably orally or parenterally, in particular perlingually or intravenously. In the case of oral use, the tablets can, of course, also contain, in addition to the excipients mentioned, additives such as sodium citrate, calcium carbonate and dicalcium phophate, together with various additional substances, such as starch, preferably potato starch, gelatine and the like. Furthermore, lubricants, such as magnesium stearate, sodium lauryl-sulphate and talc, can be co-used when making tablets. In the case of aqueous suspensions and/or elixirs which are intended for oral use, the active compounds can be mixed with various flavor-improving agents or colorants in addition to the abovementioned auxiliary substances.

In the case of parenteral use, solutions of the active compounds, employing suitable liquid excipients, can be used.

In general, it has proved advantageous, in the case of intravenous administration, to administer amounts of about 0.001 to 1 mg/kg, preferably about 0.01 to 0.5 mg/kg, of body weight daily to achieve effective results, and in the case of oral administration, the dosage is about 0.01 to 20 mg/kg, preferably 0.1 to 10 mg/kg, of body weight daily.

Nevertheless, it can at times be necessary to deviate from the amounts mentioned, and in particular to do so as a function of the body weight of the experimental animal or of the nature of the administration method, but also because of the species of animal and its individual behavior towards the medicament, and its nature of the formulation of the medicament and the time or interval over which the administration takes place. Thus it can suffice in some cases to manage with less than the above-mentioned minimum amount, whilst in other cases the upper limit mentioned must be exceeded. Where relatively large amounts are administered, it can be advisable to divide these into several individual administrations over the course of the day. The same dosage range is envisaged for administration in human medicine. The above statements also apply here in the general sense.

EXAMPLES

Example 1

Methyl 2,6-dimethyl-5-nitro-4-(2-phenyl-4-oxo-4H-chromen-8-yl)-1,4-dihydroypyridine-3-carboxylate

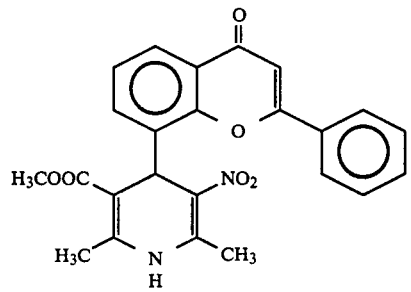

10 mmol each of 2-phenyl-4-oxo-4H-chromen-8-aldehyde, methyl 3-aminocrotonate and nitroacetone are boiled under reflux in 20 ml of absolute EtOH for 3 hours, the mixture is concentrated and the residue is crystallized from methanol.

Melting point: >260° C.

Example 2

Butyl 5-cyano-2,6-dimethyl-4-(2-phenyl-4-oxo-4H-thiochromen-8-yl)-1,4-dihydropyridine-3-carboxylate

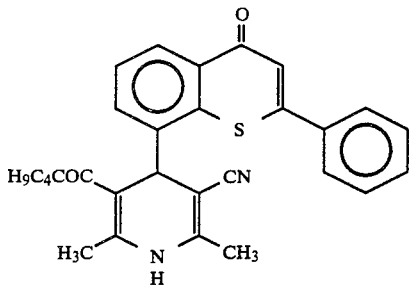

10 mmol each of 2-phenyl-4-oxo-4H-thiochromen-8-aldehyde, butyl acetoacetate and 3-aminocrotononitrile were boiled under reflux in 30 ml of ethanol overnight, the mixture was concentrated and the residue was crystallized with ethyl acetate.

Melting point: 197°–206° C.

Example 3

Methyl 2,6-dimethyl-5-nitro-4-(2-phenyl-4-oxo-4H-thiochromen-8-yl)-1,4-dihydropyridine-3-carboxylate

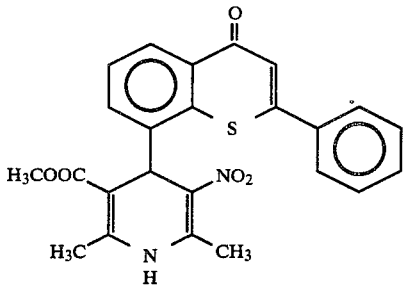

20 mmol each of 2-phenyl-4-oxo-4H-thiochromen-8-aldehyde, nitroacetone and methyl 3-aminocrotonate were boiled under reflux in 30 ml of ethanol for 3 hours, the mixture was concentrated and the residue was chromatographed on silica gel using toluene/ethyl acetate=1:1, the intensely yellow-colored spot being isolated.

Melting point 209°–211° C. (from methanol).

The following compounds were prepared analogously to Example 1 or 3

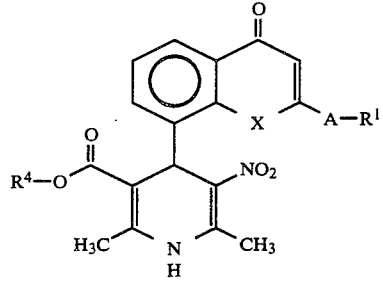

| Example | A—R$^1$ | R$^4$ | X | Melting point (°C.) | Analogous to Example: |
|---|---|---|---|---|---|
| 4 | phenyl | —C$_2$H$_5$ | S | 209–11 | 3 |
| 5 | " | —CH$_2$—CH$_2$—CH$_3$ | S | 268–70 | 3 |
| 6 | " | —(CH$_2$)$_3$—CH$_3$ | S | 209–11 | 3 |
| 7 | " | —CH$_2$—CH(CH$_3$)$_2$ | S | 205–07 | 3 |
| 8 | " | —CH$_2$—phenyl | S | 143–45 | 3 |
| 9 | " | —(CH$_2$)$_3$—CH$_3$ | S | >260 | 1 |
| 10 | cyclohexyl | —C$_2$H$_5$ | S | >250 | 1 |
| 11 | phenyl | —C$_2$H$_5$ | O | 259 | 1 |
| 12 | " | C$_3$H$_7$(n) | O | 251–53 | 1 |

-continued

| Example | A—R$^1$ | R$^4$ | X | Melting point (°C.) | Analogous to Example: |
|---|---|---|---|---|---|
| 13 | " | C$_8$H$_{17}$(n) | O | 195–200 | 1 |
| 14 | —(CH$_2$)$_8$—CH$_3$ | C$_2$H$_5$ | O | 151–155 | 1 |
| 15 | " | CH$_3$ | O | 157–162 | 1 |
| 16 | —C$_6$H$_4$—C$_4$H$_9$(n) | —C$_2$H$_5$ | O | 251–152 | 1 |
| 17 | —COOEt | —CH$_3$ | O | 233–236 | 1 |
| 18 | —C(CH$_3$)$_3$ | —CH$_3$ | O | >260 | 1 |
| 19 | " | —C$_2$H$_5$ | O | 240–244 | 1 |
| 20 | " | —C$_4$H$_9$(n) | O | 238–240 | 1 |
| 21 | —C$_6$H$_4$—C(CH$_3$)$_3$ | —C$_2$H$_5$ | O | 258–260 | 1 |
| 22 | " | —C$_4$H$_9$(n) | O | >270 | 1 |
| 23 | —(2-thienyl) | C$_2$H$_5$ | O | 247–249 | 1 |
| 24 | " | C$_4$H$_9$(n) | O | 245–247 | 1 |
| 25 | —COOC$_2$H$_5$ | C$_4$H$_9$(n) | O | 155 | 1 |
| 26 | —COOC$_2$H$_5$ | C$_2$H$_5$ | O | 120–130 | 1 |
| 27 | —(CH$_2$)$_8$—CH$_3$ | C$_4$H$_9$(n) | O | 155–157 | 1 |
| 28 | " | C$_8$H$_{17}$(n) | O | 128–132 | 1 |
| 29 | —CH$_3$ | C$_2$H$_5$ | O | 247–248 | 1 |
| 30 | —CH$_3$ | —CH$_3$ | O | >260 | 1 |
| 31 | —C$_6$H$_4$—OCH$_3$ | —C$_4$H$_9$(n) | O | >260 | 1 |
| 32 | —C$_6$H$_4$—Cl (o-Cl) | —C$_4$H$_9$(n) | O | 247–249 | 1 |
| 33 | —C$_6$H$_4$—Cl | —C$_2$H$_5$ | O | 256–257 | 1 |
| 34 | " | —CH$_3$ | O | 238–242 | 1 |
| 35 | —C$_6$H$_4$—Cl | —C$_2$H$_5$ | O | 254–257 | 1 |

The following compounds were prepared analogously to Example 2

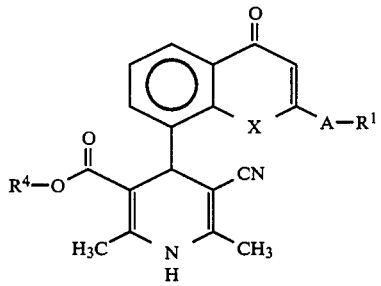

-continued

| Example | A—R¹ | R⁴ | X | Melting point (°C.) | Analogous to Example: |
|---|---|---|---|---|---|
| 36 | 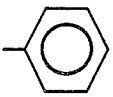 | —CH₃ | S | >270 | |
| 37 | " | —CH₂—CH₃ | S | 260–01 | |
| 38 | " | —(CH₂)₂—CH₃ | S | 212–15 | |
| 39 | " | —CH₂—CH=CH₂ | S | 226–28 | |
| 40 | " | —CH₃ | O | >280 | |
| 41 | " | —C₂H₅ | O | 267–70 | |
| 42 | (CH₂)₈—CH₃ | —C₂H₅ | O | 174–76 | |

Intermediates for the foregoing end products can be prepared as follows:

Example A

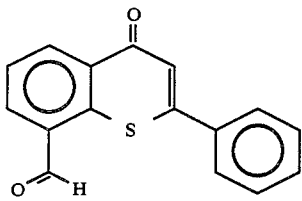 (IIa)

4 equivalents of diisobutyl aluminum hydride (in toluene) are added to 50 g of methyl thioflavone-8-carboxylate in tetrahydrofuran at 0° C., the mixture is hydrolyzed with dilute sulphuric acid, extracted with ether, and the ether is dried and evaporated.

80% of 8-hydroxymethyl-2-phenyl-4H-thiochromene (melting point: 120°–122° C.) are obtained.

20 g of 8-hydroxymethyl-2-phenyl-4H-thiochromene are dissolved in 500 ml of chloroform and heated to reflux for 10 hours with 5 equivalents of manganese dioxide, then filtered with suction and the filtrate evaporated. 60% of thioflavone-8-carboxaldehyde (melting point: 153°–157° C.) were obtained. ¹H-NMR (CDCl₃) δ=7.3 (s. 1H), 7.45–7.6 (m, 3H) 7.7–7.8 (m, 3H), 8.2 (d, J=7 Hz, 1H), 8.9 (d, J=7 Hz, 1H), 10.25 (s, 1H).

The following is prepared in analogy:

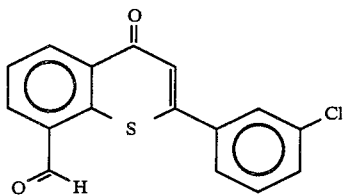 (IIb)

mp 208°–210° C.

Example B

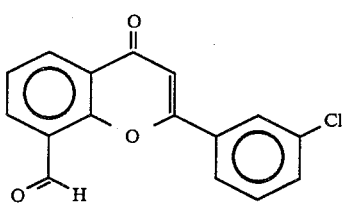 (IIc)

30 mmol of 2-(3-chlorophenyl)-4-oxo-8-propenyl-4H-chromene are dissolved in 60 ml of methylene chloride, and 30 mmol of ozone are passed in at −78° C. After addition of 100 mmol of dimethyl sulphide, the mixture is warmed to room temperature and evaporated in vacuo.

Melting point: 202°–206° C.

The following are prepared in analogy:

Intermediate II

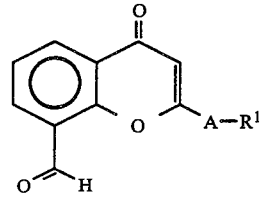

| Example | A | R¹ | Melting Point (°C.) |
|---|---|---|---|
| d | bond | phenyl | 117–119 |
| e | bond | cyclohexyl (H) | 87–89 |
| f | —(CH₂)₉— | —H | 55–60 |
| g | bond | pyridyl (N) | 100–105 |
| h | bond | phenyl—(CH₂)₃—CH₃ | oil |
| i | bond | —COOC₂H₅ | 96–99 |
| j | bond | —C(CH₃)₃ (with CH₃, CH₃, CH₃) | 67–70 |
| k | bond | phenyl—C(CH₃)₃ | 161–164 |

-continued

Intermediate II

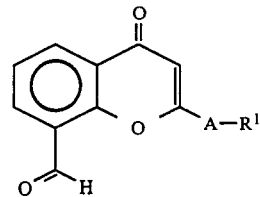

| Example | A | R¹ | Melting Point (°C.) |
|---|---|---|---|
| l | bond | (thienyl) | 161–164 |
| m | bond | —CH₃ | 157–160 |
| n | bond | —C₆H₄—OCH₃ | 200–202 |
| o | bond | —C₆H₄—Cl | 203–205 |
| p | bond | —C₆H₄—Cl | 164–170 |
| q | (—CH₂—)₂ | —(CH₂)₂—CH₃ | oil |
| r | —O—CH₂— | —C₆H₅ | 150–156 |

TEST OF THE POSITIVE INOTROPIC EFFECT

Test procedure

The left atria of guinea pig hearts are isolated and suspended in an organ bath which contains an isotonic mineral salt solution is adjusted to correspond with the ionic medium and the pH value of body fluids and also contains suitable nutrients. This organ bath is aerated with a gas mixture consisting of oxygen and carbon dioxide, the carbon dioxide content being such that the pH value of the organ bath remains constant. The left atria are fixed in the organ bath, the tension is recorded by means of a force transducer, a specific basic tonus being adjusted. Then the left atria are continuously electrically excited at specific intervals and the resulting contractions are recorded. The recording of the contractions is still carried out after the addition of the active compound. An increase of at least 25% in the contractions is considered to be a significant positive inotropic effect.

Of particular significance are those compounds of the general formula (I) which, in the following test procedure, already begin to show a positively inotropic effect on the left atria of the isolated guinea-pig hearts at a concentration of $10^{-5}$ g/ml.

The following may be mentioned as examples:

|  | Δdp/dt |
|---|---|
| Example 1 | +36% |
| Example 5 | +25% |
| Example 7 | +33% |
| Example 9 | +40% |

It will be appreciated that the instant specification and examples are set forth by way of illustration and not limitation, and that various modifications and changes may be made without departing from the spirit and scope of the present invention.

We claim:

1. A compound of the formula

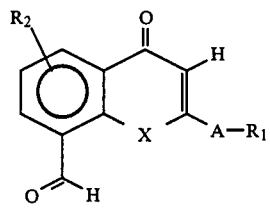

in which $R_1$ represents hydrogen, a straight-chain, cyclic or branched $C_1$–$C_{10}$ alkyl radical, a $C_1$–$C_{10}$ alkyl carboxylate, or a phenyl, 3H-thienyl; 2H-pyridyl, furyl or pyrryl radical which optionally has 1–5 identical or different halogen, $C_1$–$C_{10}$-alkyl or $C_1$–$C_{10}$-alkoxy substituents, $R_2$ represents hydrogen or 1 to 3 halogen atoms, A represents a single bond, a $C_1$–$C_{20}$ alkylene chain or a $C_2$–$C_{20}$ alkenylene chain which can optionally be interrupted by oxygen or sulphur, and X represents oxygen or sulphur.

2. A compound according to claim 1, in which $R_2$ represents hydrogen or one to three fluorine or chlorine atoms, and A represents a single bond, a $C_1$–$C_{18}$-alkylene chain or a $C_2$–$C_{18}$-alkenylene chain which can optionally be interrupted by O or S.

3. A compound according to claim 1, in which $R_2$ represents hydrogen or 1–3 fluorine atoms, and A represents a single bond, a $C_1$–$C_{16}$-alkylene radical or a $C_2$–$C_{12}$-alkenylene radical which can optionally be interrupted by O or S.

4. A compound according to claim 1, wherein such compound is

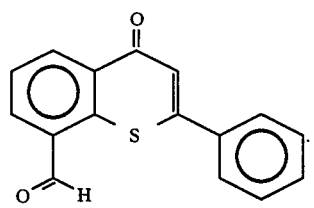

5. A compound according to claim 1, wherein such compound is

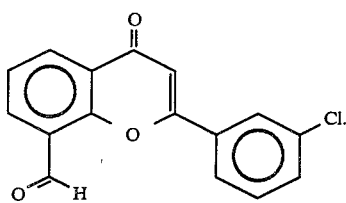
6. A compound according to claim 1, wherein such compound is
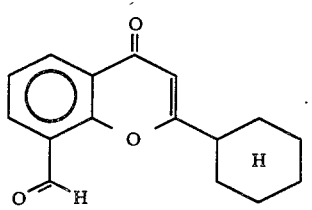
7. A compound according to claim 1, wherein such compound is
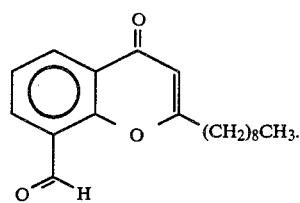
8. A compound according to claim 1, wherein such compound is
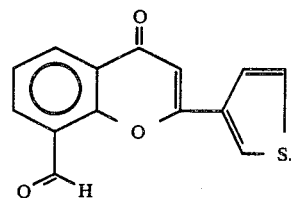
* * * * *